(12) United States Patent
Muchnik et al.

(10) Patent No.: US 12,215,811 B2
(45) Date of Patent: Feb. 4, 2025

(54) CRYOGENIC SYSTEM CONNECTOR

(71) Applicant: ICECURE MEDICAL LTD., Caesarea (IL)

(72) Inventors: Naum Muchnik, Yokneam Illit (IL); Ron Hilleli, Zichron Yaacov (IL); Shai Kaufman, Nir Eliyahu (IL); Lior Lasker, Haifa (IL); Adir Weiser, Nofit (IL)

(73) Assignee: IceCure Medical Ltd., Caesarea (IL)

( * ) Notice: Subject to any disclaimer, the term of this patent is extended or adjusted under 35 U.S.C. 154(b) by 69 days.

(21) Appl. No.: 17/866,614

(22) Filed: Jul. 18, 2022

(65) Prior Publication Data

US 2024/0019058 A1 Jan. 18, 2024

(51) Int. Cl.
*F16L 37/08* (2006.01)
*A61B 18/02* (2006.01)
*F16L 37/086* (2006.01)

(52) U.S. Cl.
CPC ............. *F16L 37/086* (2013.01); *A61B 18/02* (2013.01)

(58) Field of Classification Search
CPC ..... F16L 37/086; F16L 37/0841; F16L 55/11; F16L 2201/10; A61B 18/02; A61B 2018/0231; A61B 2018/00172; A61B 2018/0262
See application file for complete search history.

(56) References Cited

U.S. PATENT DOCUMENTS

| | | |
|---|---|---|
| 2,319,542 A | 5/1943 | Hall |
| 2,888,879 A | 6/1959 | Gaarder |
| 3,234,746 A | 2/1966 | Smith |
| 3,358,472 A | 12/1967 | Kipling |
| 3,456,595 A | 7/1969 | Gottzmann et al. |
| 3,664,344 A | 5/1972 | Bryne |

(Continued)

FOREIGN PATENT DOCUMENTS

| | | |
|---|---|---|
| CH | 265929 A | 12/1949 |
| CN | 101803947 B | 9/2012 |

(Continued)

OTHER PUBLICATIONS

Zhang et al., "Two phase flow characteristics of liquid nitrogen in vertically upward 0.5 and 1.0 mm micro-tubes: Visualization studies", Cryogenics, vol. 49, issue 10, pp. 565-575, Oct. 2009.

(Continued)

*Primary Examiner* — James M Hewitt, II
(74) *Attorney, Agent, or Firm* — Meitar Patents Ltd.; Daniel Kligler

(57) ABSTRACT

Cryogenic apparatus, consisting of a connector that has a connector base plate configured for connection to a conduit carrying a cryogen, and a slot extending across the base plate. The apparatus has a plug, which is configured for insertion into an opening in the base plate. The apparatus also has a latch plate that is configured to slide within the slot between a first position, in which the plug is inserted through an aperture in the latch plate into the opening, and a second position, in which a cryogenic probe is inserted through the aperture and brought into fluid communication with the opening. There is a sensor, which is coupled to control a flow of the cryogen through the conduit by detecting whether the latch plate is in the first position or the second position.

14 Claims, 5 Drawing Sheets

(56) References Cited

U.S. PATENT DOCUMENTS

| | | | |
|---|---|---|---|
| 3,696,813 | A | 10/1972 | Wallach |
| 3,699,775 | A | 10/1972 | Cowans |
| 3,712,306 | A | 1/1973 | Bryne |
| 3,736,936 | A | 6/1973 | Basiulis |
| 3,736,937 | A | 6/1973 | Basilius |
| 3,800,552 | A | 4/1974 | Sollami |
| 3,845,974 | A | 11/1974 | Pelloux-Gervais |
| 3,862,630 | A | 1/1975 | Balamuth |
| 3,882,849 | A | 5/1975 | Smith |
| 3,938,505 | A | 2/1976 | Jamshidi |
| 3,958,443 | A | 5/1976 | Berrettini |
| 3,971,383 | A | 7/1976 | Van Gerven |
| 3,988,029 | A | 10/1976 | Gibson |
| 4,082,096 | A | 4/1978 | Benson |
| 4,091,634 | A | 5/1978 | Shepherd |
| 4,107,946 | A | 8/1978 | Potter |
| 4,127,903 | A | 12/1978 | Schachar |
| 4,200,104 | A | 4/1980 | Harris |
| 4,202,336 | A | 5/1980 | Van Gerven |
| 4,211,231 | A | 7/1980 | Rzasa |
| 4,306,568 | A | 2/1981 | Torre |
| 4,279,626 | A | 7/1981 | Buchmuller |
| 4,313,306 | A | 2/1982 | Torre |
| 4,367,744 | A | 1/1983 | Sole |
| 4,376,376 | A | 3/1983 | Gregory |
| 4,428,748 | A | 1/1984 | Peyman |
| 4,463,458 | A | 7/1984 | Seidner |
| 4,481,948 | A | 11/1984 | Sole |
| 4,487,253 | A | 12/1984 | Malek |
| 4,541,457 | A * | 9/1985 | Blenkush ............... F16L 37/42 285/317 |
| 4,545,367 | A | 10/1985 | Tucci |
| 4,552,208 | A | 11/1985 | Sorenson |
| 4,570,626 | A | 2/1986 | Norris |
| 4,573,525 | A | 3/1986 | Boyd |
| 4,611,654 | A | 9/1986 | Buchsel |
| 4,613,112 | A * | 9/1986 | Phlipot ................... F16L 37/46 137/71 |
| 4,617,018 | A | 10/1986 | Nishi |
| 4,676,225 | A | 6/1987 | Bartera |
| 4,724,834 | A | 2/1988 | Alperovich et al. |
| 4,726,194 | A | 2/1988 | Mackay |
| 4,765,396 | A | 8/1988 | Seidenberg |
| 4,770,171 | A | 9/1988 | Sweren |
| 4,802,475 | A | 2/1989 | Weshahy |
| 4,823,790 | A | 4/1989 | Alperovich et al. |
| 4,831,856 | A | 5/1989 | Gano |
| 4,832,022 | A | 5/1989 | Tjulkov et al. |
| 4,946,460 | A | 8/1990 | Merry |
| 5,026,387 | A | 6/1991 | Thomas |
| 5,047,043 | A | 9/1991 | Kubota |
| 5,108,390 | A | 4/1992 | Potocky |
| 5,147,355 | A | 9/1992 | Friedman |
| 5,188,102 | A | 2/1993 | Idemoto |
| 5,214,925 | A | 6/1993 | Hoy |
| 5,222,937 | A | 6/1993 | Kagawa |
| 5,224,943 | A | 7/1993 | Goddard |
| 5,243,826 | A | 9/1993 | Longsworth |
| 5,254,082 | A | 10/1993 | Takase |
| 5,254,116 | A | 10/1993 | Baust |
| 5,261,923 | A | 11/1993 | Soares |
| 5,263,957 | A | 11/1993 | Davison |
| 5,264,116 | A | 11/1993 | Apelian |
| 5,267,960 | A | 12/1993 | Hayman et al. |
| 5,275,595 | A | 1/1994 | Dobak |
| 5,281,215 | A | 1/1994 | Milder |
| 5,295,484 | A | 3/1994 | Marcus |
| 5,324,286 | A | 6/1994 | Fowle |
| 5,330,745 | A | 7/1994 | Mcdow |
| 5,334,181 | A | 8/1994 | Rubinsky |
| 5,342,380 | A | 8/1994 | Hood |
| 5,361,591 | A | 11/1994 | Caldwell |
| 5,363,879 | A | 11/1994 | Rhoades |
| 5,391,144 | A | 2/1995 | Sakurai |
| 5,411,374 | A | 5/1995 | Gram |
| 5,417,073 | A | 5/1995 | James |
| 5,423,807 | A | 6/1995 | Milder |
| 5,429,138 | A | 7/1995 | Jamshidi |
| 5,429,155 | A | 7/1995 | Brzyski et al. |
| 5,438,837 | A | 8/1995 | Caldwell |
| 5,441,512 | A | 8/1995 | Muller |
| 5,445,462 | A | 8/1995 | Johnson |
| 5,452,582 | A | 9/1995 | Longsworth |
| 5,488,831 | A | 2/1996 | Griswold |
| 5,516,505 | A | 5/1996 | Mcdow |
| 5,520,682 | A | 5/1996 | Baust |
| 5,522,870 | A | 6/1996 | Ben-Zion |
| 5,526,821 | A | 6/1996 | Jamshidi |
| 5,547,473 | A | 8/1996 | Peyman |
| 5,573,532 | A | 11/1996 | Chang |
| 5,600,143 | A | 2/1997 | Roberts |
| 5,603,221 | A | 2/1997 | Maytal |
| 5,616,838 | A | 4/1997 | Preston et al. |
| 5,620,479 | A | 4/1997 | Diederich |
| 5,683,592 | A | 4/1997 | Bartholomew |
| 5,632,743 | A | 5/1997 | Clarke |
| 5,647,868 | A | 7/1997 | Chinn |
| 5,654,279 | A | 8/1997 | Rubinsky |
| 5,658,276 | A | 8/1997 | Griswold |
| 5,674,218 | A | 10/1997 | Rubinsky |
| 5,687,776 | A | 11/1997 | Forgash |
| 5,716,353 | A | 2/1998 | Matsuura |
| 5,720,743 | A | 2/1998 | Bischof |
| 5,728,130 | A | 3/1998 | Ishikawa |
| 5,735,845 | A | 4/1998 | Zupkas |
| 5,771,946 | A | 6/1998 | Kooy |
| 5,787,940 | A | 8/1998 | Bonn |
| 5,800,448 | A | 9/1998 | Banko |
| 5,800,487 | A | 9/1998 | Mikus |
| 5,814,040 | A | 9/1998 | Nelson |
| 5,860,970 | A | 1/1999 | Goddard et al. |
| 5,860,971 | A | 1/1999 | Clarke |
| 5,868,673 | A | 2/1999 | Vesely |
| 5,976,505 | A | 2/1999 | Henderson |
| 5,885,276 | A | 3/1999 | Ammar |
| 5,899,897 | A | 5/1999 | Rabin |
| 5,906,612 | A | 5/1999 | Chinn |
| 5,906,628 | A | 5/1999 | Miyawaki |
| 5,910,104 | A | 6/1999 | Dobak |
| 5,921,982 | A | 7/1999 | Lesh |
| 5,935,124 | A | 8/1999 | Klumb et al. |
| 5,946,920 | A | 9/1999 | Clarke |
| 5,957,918 | A | 9/1999 | Griswold |
| 5,976,092 | A | 11/1999 | Chinn |
| 5,992,158 | A | 11/1999 | Goddard |
| 6,007,571 | A | 12/1999 | Neilson et al. |
| 6,012,453 | A | 1/2000 | Tsais |
| 6,024,750 | A | 2/2000 | Mastri |
| 6,027,499 | A | 2/2000 | Johnston et al. |
| 6,032,068 | A | 2/2000 | Daniel |
| 6,035,646 | A | 3/2000 | Griswold |
| 6,035,657 | A | 3/2000 | Dobak |
| 6,036,667 | A | 3/2000 | Manna |
| 6,039,730 | A | 3/2000 | Rabin |
| 6,041,787 | A | 3/2000 | Rubinsky |
| 6,042,342 | A | 3/2000 | Orian |
| 6,053,906 | A | 4/2000 | Honda |
| 6,063,098 | A | 5/2000 | Houser |
| 6,074,412 | A | 6/2000 | Mikus et al. |
| 6,032,675 | A | 7/2000 | Rubinsky |
| 6,082,400 | A | 7/2000 | Tocha |
| 6,059,820 | A | 8/2000 | Baronov |
| 6,095,149 | A | 8/2000 | Sharkey |
| 6,123,675 | A | 9/2000 | Kreizman et al. |
| 6,142,991 | A | 11/2000 | Schatzberger |
| 6,145,322 | A | 11/2000 | Odashima |
| 6,152,894 | A | 11/2000 | Kubler |
| 6,182,666 | B1 | 2/2001 | Dobak |
| 6,183,019 | B1 | 2/2001 | Owen |
| 6,190,378 | B1 | 2/2001 | Jarvinen |
| 6,200,308 | B1 | 3/2001 | Pope |
| 6,203,288 | B1 | 3/2001 | Kottke |
| 6,206,832 | B1 | 3/2001 | Downey |
| 6,212,904 | B1 | 4/2001 | Arkharov |

(56) References Cited

U.S. PATENT DOCUMENTS

| | | |
|---|---|---|
| 6,216,029 B1 | 4/2001 | Paltieli |
| 6,235,018 B1 | 5/2001 | LePivert |
| 6,235,019 B1 | 5/2001 | Lehmann et al. |
| 6,237,355 B1 | 5/2001 | Li |
| 6,251,105 B1 | 6/2001 | Mikus |
| 6,270,494 B1 | 8/2001 | Kovalcheck |
| 6,280,407 B1 | 8/2001 | Manna |
| 6,354,088 B1 | 3/2002 | Emmer |
| 6,358,264 B2 | 3/2002 | Banko |
| 6,379,348 B1 | 4/2002 | Onik |
| 6,383,180 B1 | 5/2002 | Lalonde |
| 6,383,181 B1 | 5/2002 | Johnston |
| 6,411,852 B1 | 6/2002 | Danek |
| 6,413,263 B1 | 7/2002 | Lobdill |
| 6,423,009 B1 | 7/2002 | Downey |
| 6,432,102 B2 | 8/2002 | Joye |
| 6,457,212 B1 | 10/2002 | Craig |
| 6,468,268 B1 | 10/2002 | Abboud |
| 6,468,269 B1 | 10/2002 | Korpan |
| 6,471,217 B1 | 10/2002 | Hayfield |
| 6,471,694 B1 | 10/2002 | Kudaravalli et al. |
| 6,482,178 B1 | 11/2002 | Andrews |
| 6,355,033 B1 | 12/2002 | Moorman |
| 6,497,714 B1 | 12/2002 | Ishikawa |
| 6,500,109 B2 | 12/2002 | Tokita |
| 6,500,172 B1 | 12/2002 | Panescu et al. |
| 6,503,246 B1 | 1/2003 | Har-Shai |
| 6,505,629 B1 | 1/2003 | Mikus et al. |
| 6,508,814 B2 | 1/2003 | Tortal |
| 6,513,336 B2 | 2/2003 | Zurecki |
| 6,547,784 B1 | 4/2003 | Thompson |
| 6,551,309 B1 | 4/2003 | LePivert |
| 6,562,030 B1 | 5/2003 | Abboud |
| 6,565,556 B1 | 5/2003 | Korpan |
| 6,581,390 B2 | 6/2003 | Emmer |
| 6,582,425 B2 | 6/2003 | Simpson |
| 6,582,426 B2 | 6/2003 | Moorman |
| 6,659,956 B2 | 9/2003 | Barzell |
| 6,631,615 B2 | 10/2003 | Drube |
| 6,640,556 B2 | 11/2003 | Ursan |
| 6,659,730 B2 | 12/2003 | Gram |
| 6,672,095 B1 | 1/2004 | Luo |
| 6,678,621 B2 | 1/2004 | Wiener |
| 6,682,525 B2 | 1/2004 | Lalonde |
| 6,698,423 B1 | 3/2004 | Honkonen |
| 6,702,761 B1 | 3/2004 | Damadian |
| 6,706,037 B2 | 3/2004 | Zvuloni et al. |
| 6,761,715 B2 | 7/2004 | Carroll |
| 6,765,333 B1 | 7/2004 | Mariaucue |
| 6,768,917 B1 | 7/2004 | Van Vaals |
| 6,772,766 B2 | 8/2004 | Gallo |
| 6,786,902 B1 | 9/2004 | Rabin |
| 6,789,545 B2 | 9/2004 | Littrup et al. |
| 6,824,543 B2 | 11/2004 | Lentz |
| 6,852,110 B2 | 2/2005 | Roy et al. |
| 6,852,706 B1 | 2/2005 | Heber-Katz |
| 6,858,025 B2 | 2/2005 | Maurice |
| 6,866,624 B2 | 3/2005 | Chornenky et al. |
| 6,869,439 B2 | 3/2005 | White |
| 6,889,695 B2 | 5/2005 | Pankratov |
| 6,898,940 B2 | 5/2005 | Gram |
| 6,908,472 B2 | 6/2005 | Wiener |
| 6,910,510 B2 | 6/2005 | Gale |
| 6,913,604 B2 | 7/2005 | Mihalik |
| 6,918,869 B2 | 7/2005 | Shaw et al. |
| 6,929,639 B2 | 8/2005 | Lafontaine |
| 6,932,771 B2 | 8/2005 | Whitmore |
| 6,936,045 B2 | 8/2005 | Yu |
| 6,939,346 B2 | 9/2005 | Kannenberg et al. |
| 6,942,659 B2 | 9/2005 | Lehmann |
| 6,945,477 B2 | 9/2005 | Lambert et al. |
| 6,951,569 B2 | 10/2005 | Nohilly |
| 6,954,977 B2 | 10/2005 | Maguire |
| 6,995,493 B2 | 2/2006 | Soda |
| 7,001,378 B2 | 2/2006 | Yon |
| 7,025,762 B2 | 4/2006 | Johnston |
| 7,025,767 B2 | 4/2006 | Schaefer |
| 7,101,367 B2 | 5/2006 | Xiao |
| 7,071,690 B2 | 7/2006 | Butts |
| 7,081,111 B2 | 7/2006 | Svaasand |
| 7,083,612 B2 | 8/2006 | Littrup et al. |
| 7,128,347 B2 | 10/2006 | Kerin |
| 7,128,738 B2 | 10/2006 | Littrup et al. |
| 7,128,739 B2 | 10/2006 | Prakash |
| 7,137,978 B2 | 11/2006 | Levin |
| 7,144,228 B2 | 12/2006 | Emmer |
| 7,151,374 B2 | 12/2006 | Doty |
| 7,156,840 B2 | 1/2007 | Lentz et al. |
| 7,160,291 B2 | 1/2007 | Damasco |
| 7,160,292 B2 | 1/2007 | Moorman |
| 7,165,422 B2 | 1/2007 | Little |
| 7,189,228 B2 | 3/2007 | Eum |
| 7,192,426 B2 | 3/2007 | Baust et al. |
| 7,250,046 B1 | 3/2007 | Fallat |
| 7,207,985 B2 | 4/2007 | Duong |
| 7,213,400 B2 | 5/2007 | Dickerson |
| 7,223,080 B2 | 5/2007 | Duron |
| 7,252,648 B2 | 8/2007 | Honda |
| 7,255,693 B1 | 8/2007 | Johnston |
| 7,273,479 B2 | 9/2007 | Littrup |
| 7,278,991 B2 | 10/2007 | Morris |
| 7,280,623 B2 | 10/2007 | Gupta |
| 7,282,919 B2 | 10/2007 | Doty |
| 7,288,089 B2 | 10/2007 | Yon |
| 7,318,327 B2 | 1/2008 | Dickerson |
| 7,344,530 B2 | 3/2008 | Bischof |
| 7,344,531 B2 | 3/2008 | Bischof |
| 7,354,434 B2 | 4/2008 | zvuloni |
| 7,357,797 B2 | 4/2008 | Ryba |
| 7,361,187 B2 | 4/2008 | Duong |
| 7,381,207 B2 | 6/2008 | Duong |
| 7,407,501 B2 | 8/2008 | Zvuloni |
| 7,422,583 B2 | 9/2008 | Maurice |
| 7,425,211 B2 | 9/2008 | Levin et al. |
| 7,458,379 B2 | 12/2008 | Littrup et al. |
| 7,458,968 B2 | 12/2008 | Carroll |
| 7,469,718 B2 * | 12/2008 | Lambert ............... A61M 16/08 |
| | | 62/50.7 |
| 7,481,806 B2 | 1/2009 | Levin |
| 7,485,117 B2 | 2/2009 | Damasco |
| 7,498,812 B2 | 3/2009 | Doty |
| 7,510,554 B2 | 3/2009 | Duong |
| 7,563,260 B2 | 7/2009 | Whitmore |
| 7,568,735 B2 * | 8/2009 | Akiba ..................... A61B 1/12 |
| | | 285/317 |
| 7,731,711 B2 | 6/2010 | Levin |
| 7,780,657 B2 | 8/2010 | Abboud et al. |
| 7,803,154 B2 | 9/2010 | Toubia et al. |
| 7,921,657 B2 | 4/2011 | Littrup et al. |
| 7,938,822 B1 | 5/2011 | Berzak et al. |
| 7,967,814 B2 | 6/2011 | Levin |
| 7,967,815 B1 | 6/2011 | Berzak et al. |
| 8,080,005 B1 | 12/2011 | Berzak et al. |
| 8,092,448 B2 | 1/2012 | DeLonzor |
| 8,162,812 B2 | 4/2012 | Shai et al. |
| 8,187,264 B2 | 5/2012 | Kobayashi |
| 8,348,855 B2 | 1/2013 | Hillely et al. |
| 8,418,480 B2 | 4/2013 | Danley et al. |
| 8,475,448 B2 | 7/2013 | Sharareh et al. |
| 8,500,173 B2 * | 8/2013 | Zahler ............... A61B 1/00128 |
| | | 285/308 |
| 8,517,749 B2 | 8/2013 | Marshall |
| 8,551,081 B2 | 10/2013 | Baust et al. |
| 8,579,892 B2 | 11/2013 | Hoey et al. |
| 8,591,505 B2 | 11/2013 | Sharon et al. |
| 8,671,700 B2 | 3/2014 | Duong et al. |
| 8,685,014 B2 | 4/2014 | Babkin et al. |
| 8,709,005 B2 | 4/2014 | Berzak et al. |
| 8,784,409 B2 | 7/2014 | Robilotto et al. |
| 8,814,850 B2 | 8/2014 | Babkin et al. |
| 8,845,628 B2 | 9/2014 | Babkin et al. |
| 8,906,004 B2 | 12/2014 | Berzak et al. |
| 8,998,888 B2 | 4/2015 | Baust et al. |
| 9,039,689 B2 | 5/2015 | Berzak et al. |

(56) References Cited

U.S. PATENT DOCUMENTS

| | | |
|---|---|---|
| 9,050,072 B2 | 6/2015 | Delonzor et al. |
| 9,050,075 B2 | 6/2015 | Berzak et al. |
| 9,101,343 B2 | 8/2015 | Duong et al. |
| 9,125,689 B2 | 9/2015 | Mielekamp |
| 9,144,461 B2 | 9/2015 | Kruecker et al. |
| 9,157,560 B2 | 10/2015 | Rehder et al. |
| 9,237,919 B2 | 1/2016 | Maschke |
| 9,316,215 B2 | 4/2016 | Mackey |
| 9,408,654 B2 | 8/2016 | Baust et al. |
| 9,441,997 B2 | 9/2016 | Downie et al. |
| 9,808,302 B2 | 11/2017 | Berzak et al. |
| 9,956,024 B2 | 5/2018 | Mahrouche et al. |
| 10,022,175 B2 | 7/2018 | Abboud et al. |
| 10,054,262 B2 | 8/2018 | Baust et al. |
| 10,098,685 B2 | 10/2018 | Lalonde et al. |
| 10,125,771 B2 | 11/2018 | Caldwell et al. |
| 10,159,522 B2 | 12/2018 | Littrup et al. |
| 10,213,244 B2 | 2/2019 | Fourkas et al. |
| 10,363,081 B2 | 7/2019 | Clarke |
| 10,383,686 B2 | 8/2019 | Panescu et al. |
| 10,390,871 B2 | 8/2019 | Ramadhyani et al. |
| 10,485,602 B2 | 11/2019 | Geiselhart |
| 10,531,656 B2 | 1/2020 | Schryver |
| 10,702,251 B2 | 7/2020 | Nevo |
| 10,828,080 B2 | 11/2020 | George et al. |
| 10,859,211 B2 | 12/2020 | Bollinger |
| 11,026,737 B2 | 6/2021 | Baust et al. |
| 11,060,778 B2 | 7/2021 | Jankowsky et al. |
| 11,266,458 B2 | 3/2022 | Perron et al. |
| 2001/0047129 A1 | 11/2001 | Hall |
| 2002/0016540 A1 | 2/2002 | Mikus |
| 2002/0022832 A1 | 2/2002 | Mikus |
| 2002/0040220 A1 | 4/2002 | Zvuloni |
| 2002/0042609 A1 | 4/2002 | Kelman et al. |
| 2002/0077654 A1 | 6/2002 | Javier |
| 2002/0085921 A1 | 7/2002 | Gram |
| 2002/0144509 A1 | 10/2002 | Chalk |
| 2002/0156469 A1 | 10/2002 | Yon |
| 2002/0157402 A1 | 10/2002 | Drube |
| 2002/0160640 A1 | 10/2002 | Korpan |
| 2002/0161385 A1 | 10/2002 | Wiener |
| 2003/0060762 A1 | 3/2003 | Zvuloni |
| 2003/0079480 A1 | 5/2003 | Emmer |
| 2003/0126867 A1 | 7/2003 | Drube |
| 2003/0135119 A1 | 7/2003 | Lee |
| 2003/0181897 A1 | 9/2003 | Thomas |
| 2003/0220635 A1 | 11/2003 | Knowlton |
| 2004/0024391 A1 | 2/2004 | Cytron |
| 2004/0024392 A1 | 2/2004 | Lewis et al. |
| 2004/0055316 A1 | 3/2004 | Emmer |
| 2004/0078033 A1 | 4/2004 | Levin |
| 2004/0106841 A1 | 6/2004 | Shaw et al. |
| 2004/0210212 A1 | 10/2004 | Maurice |
| 2004/0215178 A1 | 10/2004 | Maurice |
| 2005/0016185 A1 | 1/2005 | Emmer |
| 2005/0038422 A1 | 2/2005 | Maurice |
| 2005/0043725 A1 | 2/2005 | Duong et al. |
| 2005/0056027 A1 | 3/2005 | White |
| 2005/0086949 A1 | 4/2005 | Noble |
| 2005/0106153 A1 | 5/2005 | Nordouist |
| 2005/0159735 A1 | 7/2005 | Walton et al. |
| 2005/0177147 A1 | 8/2005 | Vancelette |
| 2005/0192564 A1 | 9/2005 | Cosman |
| 2005/0198972 A1 | 9/2005 | Lentz et al. |
| 2005/0214268 A1 | 9/2005 | Cavanagh |
| 2005/0274127 A1 | 12/2005 | Drube et al. |
| 2005/0274142 A1 | 12/2005 | Corey |
| 2005/0288658 A1 | 12/2005 | Littrup et al. |
| 2006/0049274 A1 | 3/2006 | Hume |
| 2006/0053165 A1 | 3/2006 | Hume |
| 2006/0079867 A1 | 4/2006 | Berzak |
| 2006/0100495 A1 | 5/2006 | Santoianni et al. |
| 2006/0122590 A1 | 6/2006 | Bliweis |
| 2006/0155267 A1 | 7/2006 | Berzak |
| 2006/0155268 A1 | 7/2006 | Amir |
| 2006/0253114 A1 | 11/2006 | Saadat |
| 2006/0264920 A1 | 11/2006 | Duong |
| 2006/0293647 A1 | 12/2006 | McRae |
| 2007/0000259 A1 | 1/2007 | Brook |
| 2007/0043342 A1 | 2/2007 | Kleinberger |
| 2007/0088217 A1 | 4/2007 | Babaev |
| 2007/0093710 A1 | 4/2007 | Maschke |
| 2007/0123815 A1 | 5/2007 | Mark |
| 2007/0129626 A1 | 6/2007 | Mahesh |
| 2007/0129629 A1 | 6/2007 | Beauregard |
| 2007/0149959 A1 | 6/2007 | DeLonzor |
| 2007/0153969 A1 | 7/2007 | Maschke |
| 2007/0166171 A1 | 7/2007 | Kondo |
| 2007/0167939 A1 | 7/2007 | Duong |
| 2007/0244474 A1 | 10/2007 | DeLonzor et al. |
| 2007/0276360 A1 | 11/2007 | Johnston |
| 2007/0277550 A1 | 12/2007 | Li et al. |
| 2008/0027419 A1 | 1/2008 | Hamel |
| 2008/0039745 A1 | 2/2008 | Babaev |
| 2008/0051774 A1 | 2/2008 | Ofir |
| 2008/0051776 A1 | 2/2008 | Bliweis |
| 2008/0097251 A1 | 4/2008 | Babaev |
| 2008/0114344 A1 | 5/2008 | Xiao et al. |
| 2008/0114346 A1 | 5/2008 | Levin et al. |
| 2008/0115509 A1 | 5/2008 | Gullickson |
| 2008/0119834 A1 | 5/2008 | Vancelette |
| 2008/0119838 A1 | 5/2008 | Vancelette |
| 2008/0125764 A1 | 5/2008 | Vancelette et al. |
| 2008/0140061 A1 | 6/2008 | Toubia et al. |
| 2008/0319433 A1 | 12/2008 | Geiselhart |
| 2009/0011032 A1 | 1/2009 | LePivert |
| 2009/0149957 A1 | 6/2009 | Ross et al. |
| 2009/0163902 A1 | 6/2009 | DeLonzor et al. |
| 2009/0182320 A1 | 7/2009 | DeLonzor et al. |
| 2009/0192505 A1 | 7/2009 | Askew et al. |
| 2010/0057063 A1 | 3/2010 | Arless et al. |
| 2010/0256621 A1 | 10/2010 | Babkin et al. |
| 2010/0256622 A1* | 10/2010 | Baust .............. F25B 19/005 |
| | | 606/23 |
| 2010/0256642 A1 | 10/2010 | Stone |
| 2011/0082351 A1 | 4/2011 | Razzaque et al. |
| 2011/0306958 A1 | 12/2011 | Berzak et al. |
| 2012/0007352 A1* | 1/2012 | Nguyen .............. A61M 39/12 |
| | | 285/308 |
| 2012/0316558 A1 | 12/2012 | Hendriks et al. |
| 2013/0103020 A1 | 4/2013 | Levin |
| 2014/0169993 A1 | 6/2014 | Berzak et al. |
| 2014/0194863 A1 | 7/2014 | Berzak et al. |
| 2014/0350537 A1 | 11/2014 | Baust et al. |
| 2015/0126987 A1 | 5/2015 | Semenov et al. |
| 2015/0300344 A1 | 10/2015 | Berzak et al. |
| 2016/0135864 A1 | 5/2016 | Babkin et al. |
| 2016/0249970 A1 | 9/2016 | Yu et al. |
| 2019/0175395 A1 | 6/2019 | Kim |
| 2019/0254731 A9 | 8/2019 | Sperling et al. |
| 2019/0290348 A1 | 9/2019 | Clarke |
| 2019/0328437 A1 | 10/2019 | Perron et al. |
| 2019/0390822 A1 | 12/2019 | Brothers |
| 2020/0015750 A1 | 1/2020 | Pike et al. |
| 2020/0121498 A1 | 4/2020 | Baust et al. |
| 2020/0297403 A1 | 9/2020 | Kochavi |
| 2020/0378556 A1 | 12/2020 | Wowk et al. |
| 2021/0177482 A1 | 6/2021 | Tegg et al. |
| 2021/0177483 A1 | 6/2021 | Tegg et al. |
| 2021/0239257 A1 | 8/2021 | Stautner |
| 2021/0244457 A1 | 8/2021 | Hilleli et al. |
| 2021/0369319 A1 | 12/2021 | Sprain et al. |
| 2021/0396336 A1 | 12/2021 | Schroeter |
| 2022/0287757 A1 | 9/2022 | Gong et al. |
| 2022/0304737 A1 | 9/2022 | Pang et al. |
| 2023/0213129 A1* | 7/2023 | Peabody .............. A61M 39/18 |

FOREIGN PATENT DOCUMENTS

| | | |
|---|---|---|
| CN | 102488550 B | 4/2013 |
| CN | 203122580 U | 8/2013 |
| CN | 203641719 U | 6/2014 |
| CN | 203873871 U | 10/2014 |
| CN | 204219026 U | 3/2015 |

(56) References Cited

FOREIGN PATENT DOCUMENTS

| | | |
|---|---|---|
| CN | 104605925 A | 5/2015 |
| CN | 204797984 U | 11/2015 |
| CN | 103784193 B | 12/2015 |
| CN | 207870952 U | 9/2018 |
| CN | 208511163 U | 2/2019 |
| CN | 208541399 U | 2/2019 |
| CN | 109431595 B | 3/2019 |
| CN | 109674525 A | 4/2019 |
| CN | 208677560 U | 4/2019 |
| CN | 208693430 U | 4/2019 |
| CN | 209032618 U | 6/2019 |
| CN | 109984734 A | 7/2019 |
| CN | 209059412 U | 7/2019 |
| CN | 209153957 U | 7/2019 |
| CN | 209301311 U | 8/2019 |
| CN | 209326130 U | 8/2019 |
| CN | 110236671 A | 9/2019 |
| CN | 209360883 U | 9/2019 |
| CN | 209470383 U | 10/2019 |
| CN | 209574862 U | 11/2019 |
| CN | 209751207 U | 12/2019 |
| CN | 209826947 U | 12/2019 |
| CN | 209826949 U | 12/2019 |
| CN | 209842088 U | 12/2019 |
| CN | 209847361 U | 12/2019 |
| CN | 110251224 B | 2/2020 |
| CN | 210019627 U | 2/2020 |
| CN | 210019628 U | 2/2020 |
| CN | 210056206 U | 2/2020 |
| CN | 211094644 U | 7/2020 |
| CN | 213216941 U | 5/2021 |
| CN | 214010591 U | 8/2021 |
| DE | 202004008875 U1 | 8/2004 |
| EP | 0292922 B1 | 11/1988 |
| EP | 395307 A2 | 10/1990 |
| EP | 570301 A1 | 11/1994 |
| EP | 0550666 B1 | 1/1999 |
| EP | 919197 B1 | 2/2005 |
| EP | 2593028 B1 | 8/2017 |
| EP | 2904986 B1 | 7/2022 |
| GB | 1108905 A | 4/1968 |
| GB | 1473856 A | 5/1977 |
| GB | 1534472 A | 12/1978 |
| GB | 2321531 A | 7/1998 |
| GB | 2336781 A | 11/1999 |
| GB | 2337000 A | 11/1999 |
| GB | 2409815 A1 | 7/2005 |
| JP | 2004041428 A1 | 2/2004 |
| JP | 2004275732 A | 10/2004 |
| JP | 2007167100 A | 7/2007 |
| WO | 8303961 A1 | 11/1983 |
| WO | 9637158 A1 | 11/1996 |
| WO | 9639960 A1 | 12/1996 |
| WO | 9947876 A1 | 9/1999 |
| WO | 200137919 A2 | 5/2001 |
| WO | 200141683 A3 | 6/2001 |
| WO | 200197702 A1 | 12/2001 |
| WO | 0202026 A1 | 1/2002 |
| WO | 0211638 A1 | 2/2002 |
| WO | 03015651 A1 | 2/2003 |
| WO | 2004051409 A2 | 6/2004 |
| WO | 2004060465 A2 | 7/2004 |
| WO | 2004089183 A1 | 10/2004 |
| WO | 2004093635 A2 | 11/2004 |
| WO | 2005000106 A2 | 1/2005 |
| WO | 2005098308 A1 | 10/2005 |
| WO | 2006116457 A2 | 11/2006 |
| WO | 2006127467 A2 | 11/2006 |
| WO | 2007028232 A1 | 3/2007 |
| WO | 2007076123 A2 | 7/2007 |
| WO | 2007086056 A2 | 8/2007 |
| WO | 2007129308 A2 | 11/2007 |
| WO | 2013067421 A2 | 5/2013 |
| WO | 2014068262 A1 | 5/2014 |
| WO | 2014137383 A1 | 9/2014 |
| WO | 2018184938 A1 | 10/2018 |
| WO | 2019077508 A1 | 4/2019 |
| WO | 2021027682 A1 | 2/2021 |
| WO | 2021258840 A1 | 12/2021 |

OTHER PUBLICATIONS

Qi et al., "Development and performance test of a cryoprobe with heat transfer enhancement configuration", Cryogenics, vol. 46, pp. 881-887, year 2006.
Qi et al., "Flow boiling of liquid nitrogen in micro-tubes: Part I—onset of nucleate boiling, two phase flow instability and two phase flow pressure drop", International Journal of Heat and Mass Transfer, vol. 50, pp. 4999-5016, year 2007.
Qi et al., "Flow boiling of liquid nitrogen in micro-tubes: Part II—heat transfer characteristics and critical heat flux", International Journal of Heat and Mass Transfer, vol. 50, pp. 5017-5030, year 2007.
Li et al., "A Compact Cryogenic Pump," Elsevier, open-access version, pp. 1-6, year 2015.
Verkin et al., "Low Temperatures in Stomatology," Naukova Dumka, Kiev, pp. 62-63, year 1990.
JP Application # 202112530 Office Action dated Aug. 23, 2022.
U.S. Appl. No. 16/785,686 Office Action dated Sep. 16, 2022.
EP Application # 22174876.7 Search Report dated Nov. 4, 2022.
Castillo-Dominguez et al., "Cryostat and CCD for MEGARA at GTC," Conference Paper in Proceedings of SPIE—The International Society for Optical Engineering, pp. 2-11, Sep. 2012.
Douglas, Jr., et al, "Cryosurgial Denervation of the Heart: Acute and Chronic Effects," The Journal of Thoracic and Cardiovascular Surgery, vol. 100, pp. 198-209, year 1990.
JP Application # 2022091916 Office Action dated Nov. 22, 2023.
EP Application # 23180921.1 Search Report dated Nov. 22, 2023.
EP Application # 23172909.6 Search Report dated Oct. 5, 2023.
Hilleli et al., U.S. Appl. No. 17/681,868, filed Feb. 28, 2022.
Hilleli et al., U.S. Appl. No. 17/828,128, filed May 31, 2022.
EP Application # 23172909.6 Search Report dated Apr. 17, 2024.
JP Application # 2023115854 Office Action dated May 14, 2024.
U.S. Appl. No. 18/184,693 Office Action dated May 23, 2024.
JP Application # 2023088275 Office Action dated Jun. 4, 2024.

\* cited by examiner

CRYOGENIC SYSTEM CONNECTOR

FIELD OF THE INVENTION

This invention relates generally to cryogenics, and specifically to connecting entities used in a cryogenic system together.

BACKGROUND OF THE INVENTION

Entities used in a cryogenic system, such as a Dewar or a medical probe, are typically well-insulated to reduce evaporation of cryogen, and are also typically well-sealed to prevent ingress of elements such as moisture. In order to connect the entities, any connector should provide the same properties of good insulation and sealing, while permitting connection and disconnection of the entities.

U.S. Pat. No. 3,845,974, to Pelloux, describes a coupling device for a line conduit conveying cryogenic liquids. The device is stated to be of the easy make-and-break type and to comprise two connectable coupling bodies.

U.S. Pat. No. 3,988,029, to Gibson, describes a coupling device for cryogenic fluids which allows passage of liquid and vapor simultaneously through one coaxially arranged assembly. The device is stated to have low heat transfer insulation integral with the coupling and also the ability to connect and disconnect without use of tools.

U.S. Pat. No. 4,107,946, to Potter, describes an interface for a magnet Dewar which includes a low leakage disconnect fitting that retains the vacuum integrity of both the Dewar and a connected transfer line.

U.S. Pat. No. 5,363,879, to Rhoades, describes a coupling assembly for dispensing cryogenic fluids. The assembly has an upstream terminus coupled to a source of cryogenic fluid and a downstream terminus connected to a container for receiving the cryogenic fluid. A poppet valve assembly is disposed at the upstream dispensing terminus.

U.S. Pat. No. 5,429,155, to Brzyski et al, describes a cryogenic fluid coupling that has a male half and a female half. Each half has a poppet valve arranged to move toward and way from a seat. The male half has an outer sleeve which is adapted to guide initial joinder of the female half distal end.

U.S. Pat. No. 5,452,582, to Longsworth, describes a cryo-probe wherein refrigerant is furnished from a high pressure, room temperature supply. Refrigerant flows through a pre-cooling heat exchanger in the probe and through a restrictor wherein the pressure drops.

U.S. Pat. No. 5,946,920, to Clarke, describes controlling the flow rate of a liquid cryogen by controlling variably the pressure propellant gas acting directly or indirectly on the liquid cryogen.

U.S. Pat. No. 5,957,918, to Griswold, describes a cryosurgical instrument having a Dewar and a cap which is threaded onto the Dewar when in use, with a main valve portion secured to the cap by threads. The handedness of the threads on the main valve portion are opposite to the handedness of the cap threads.

U.S. Pat. No. 6,035,646, to Griswold, describes a liquid cryogen withdrawal device that includes a plug for insertion into the neck of a cryogen-containing Dewar in a gas-tight relationship.

U.S. Pat. No. 6,082,400, to Tocha, describes a coupling for connecting vacuum-insulated line ends via a coupling socket and a coupling plug. The socket and the plug are provided for conveying a cryogenic medium and have closing elements.

U.S. Pat. No. 6,145,322, to Odashima, describes a cryogenic coupler that includes a socket and a plug that can be detachably inserted into the socket. The socket and the plug have passages for passing a cryogenic medium therethrough, and are provided with valves for blocking the respective passages when the plug is disconnected from the socket.

U.S. Pat. No. 6,183,019, to Owen, describes a coupling device that can connect two cryogenic fluid conduits in fluid communication without creating a temperature change. The coupling device is stated to have a fluid flow path with a substantially constant cross-sectional area. The coupling device is stated to be designed to be easy to connect and disconnect and to provide a secure connection, in particular at a low temperature.

U.S. Pat. No. 6,945,477, to Lambert et al, describes a cryogenic coupling device that includes a valved receptacle and a valved nozzle. Rollers in an outer collar of the receptacle are received in helical channels along a collar of the nozzle. A notch or detent in each of the channels provides a vent position to vent fluid before the nozzle is fully disconnected from the receptacle.

U.S. Pat. No. 7,128,347, to Kerin, describes a quick connector coupling for forming a joint in a fluid line system. The quick connector coupling has a female connector body, a male member and a latch coupled to the connector body.

U.S. Pat. No. 7,189,228, to Eum et al, describes a disposable probe assembly that includes a breakaway collar. The collar, when twisted away, activates a finger lock element.

U.S. Pat. No. 7,381,207, to Duong et al, describes a quick disconnect assembly that includes a reusable assembly including a distal end having a male lip. There is a disposable assembly having quick disconnect capabilities when utilized with the reusable assembly.

U.S. Pat. No. 7,469,718, to Lambert et al, describes a cylindrical quick disconnect female cryogenic coupler, interconnected with a cryogenic fluid transfer apparatus. The coupler includes a coupler body with a first cavity housing a laterally severed tubular bushing, and an adaptor having one end attached to the coupler body and another end to the apparatus.

U.S. Pat. No. 8,092,448, to DeLonzor, describes a liquid cryogen fluid system for providing cryogenic liquid to a cryoprobe. Flow of cryogen from a cryogen source to the cryoprobe is induced by pressurizing the cryogen source with air delivered by a pressurization pump.

U.S. Pat. No. 8,517,749, to Marshall, describes an apparatus that enables quick disconnect termination or connection for cryogenic transfer lines. The apparatus is a connector that will allow two lines to be connected and coupled to simultaneously allow fluid flow to occur and electrical communication to ensue. The connection and termination are stated to occur successfully under a pressurized environment.

U.S. Pat. No. 8,784,409, to Robilotto et al, describes a cryogenic medical device for delivery of subcooled liquid cryogen to various configurations of cryoprobes. The device is a closed or semi-closed system in which the liquid cryogen is contained in both the supply and return stages.

U.S. Pat. No. 10,022,175, to Abboud et al, describes a first pliable element defining a cooling chamber and a second pliable element which partially encloses the first pliable element, thereby defining a junction between the first and second pliable element. A check valve is included which is in fluid communication with the junction.

U.S. Pat. No. 10,054,262, to Baust et al, describes a cryogenic system that includes a reservoir containing a liquid cryogen and a sub-cooling coil immersed in the liquid cryogen. The cryogen is supplied to the sub-cooling coil and is cooled under pressure to produce a pressurized mixed phase cryogen within the sub-cooling coil. This pressurized mixed phase cryogen is provided via a supply line to a cryo-device for use by the device.

U.S. Pat. No. 10,159,522, to Littrup et al, describes a device, for freezing body tissue, having a main driving system capable of generating nitrogen under physical conditions near a critical point of a liquid-vapor system for the nitrogen.

U.S. Pat. No. 10,531,656, to Schryver, describes a liquid nitrogen delivery and flow regulation system that may be used to regulate the temperature of a cold cavity. Liquid nitrogen is delivered to a liquid nitrogen boiler from a storage Dewar. The Dewar is filled through a coupling connector attached to a feed-line that enters into a manifold. Liquid nitrogen inflow to the Dewar is regulated by an electrically controlled valve that receives signals from a control board on a control line. During the Dewar filling cycle, internal back-pressure in the Dewar is released by an electrically controlled gas release valve that is operated by a signal control line.

U.S. Pat. No. 10,859,211, to Bollinger, describes a vapor plug, which partially seals an opening of a Dewar. The vapor plug includes a vapor plug cover which is configured to cover an opening of the Dewar. The vapor plug includes a neck that is formed from multiple disks and multiple sheets. The vapor plug includes a fastener that connects the multiple disks, the multiple sheets and the vapor plug cover.

U. S. Patent Application 2004/0024392, to Lewis et al, describes apparatus for delivery of cryosurgery fluid in a surgical or other medical environment. The apparatus comprises a multiple-layered expanded polytetrafluoroethylene conduit that has a low profile, has low thermal conductivity, and is stated to provide exceptional flexibility.

U. S. Patent Application 2019/0390822, to Brothers, describes a supply line that supplies cryogenic liquid to a plurality of cryogenic freezers. A fill line having a diameter greater than the supply line allows a storage tank to be filled at a greater speed relative to filling through the supply line and allows the storage tank to be filled while supplying cryogenic liquid to the cryogenic freezers.

Chinese Patent CN203641719U, to WU JIANNAN, describes a connector connecting a gas storage tank and a Dewar. The connector has a threaded sleeve piece used for connecting with a fluid outlet of the gas storage tank. There is a corresponding connector body used for filling of the Dewar.

U. K. Patent GB2321531A, to Cutler, describes an infrared radiation detector having a Dewar type vessel. The detector has a coupler which is coupled to the wall of the vessel. The coupler includes a fibre which can transmit infra red radiation and which terminates close to a detector provided in the Dewar type vessel

SUMMARY OF THE INVENTION

An embodiment of the present invention provides cryogenic apparatus, consisting of:
a connector having:
a connector base plate configured for connection to a conduit carrying a cryogen; and
a slot extending across the base plate;
a plug, which is configured for insertion into an opening in the base plate;
a latch plate configured to slide within the slot between a first position, in which the plug is inserted through an aperture in the latch plate into the opening, and a second position, in which a cryogenic probe is inserted through the aperture and brought into fluid communication with the opening; and
a sensor, which is coupled to control a flow of the cryogen through the conduit by detecting whether the latch plate is in the first position or the second position.

In a disclosed embodiment the plug has a groove, and the aperture grips the groove, when the plug is inserted through the aperture, so as to lock the plug to the latch plate.

In another disclosed embodiment the cryogenic probe has a groove, and the aperture grips the groove, when the probe is inserted through the aperture, so as to lock the probe to the latch plate.

In yet another disclosed embodiment there is a control rod which penetrates a further aperture in the latch plate and which is configured to operate the sensor.

In an alternative embodiment there is a control rod which penetrates a further aperture in the latch plate and which, when the latch plate is in the first position, is in a first control rod position that deactivates the sensor so as to prevent flow of the cryogen, and when the latch plate is in the second position, is in a second control rod position that activates the sensor so as to permit flow of the cryogen.

In another alternative embodiment there is a control rod which penetrates a further aperture in the latch plate and which, when the latch plate is in the first position, is in a first control rod position that prevents the latch plate from moving from the first position, and when the latch plate is in the second position, is in a second control rod position that prevents the latch plate from moving from the second position. Typically, the control rod, when translated from the first control rod position permits the latch plate moving from the first position, and, when translated from the second control rod position permits the latch plate moving from the second position.

There is further provided, according to an embodiment of the present invention, a method, including:
providing a connector having:
a connector base plate configured for connection to a conduit carrying a cryogen; and
a slot extending across the base plate;
configuring a plug for insertion into an opening in the base plate;
sliding a latch plate within the slot between a first position, in which the plug is inserted through an aperture in the latch plate into the opening, and a second position, in which a cryogenic probe is inserted through the aperture and brought into fluid communication with the opening; and
coupling a sensor to control a flow of the cryogen through the conduit by detecting whether the latch plate is in the first position or the second position.

The present disclosure will be more fully understood from the following detailed description of the embodiments thereof, taken together with the drawings, in which:

DETAILED DESCRIPTION OF EMBODIMENTS

Overview

Figure 1:
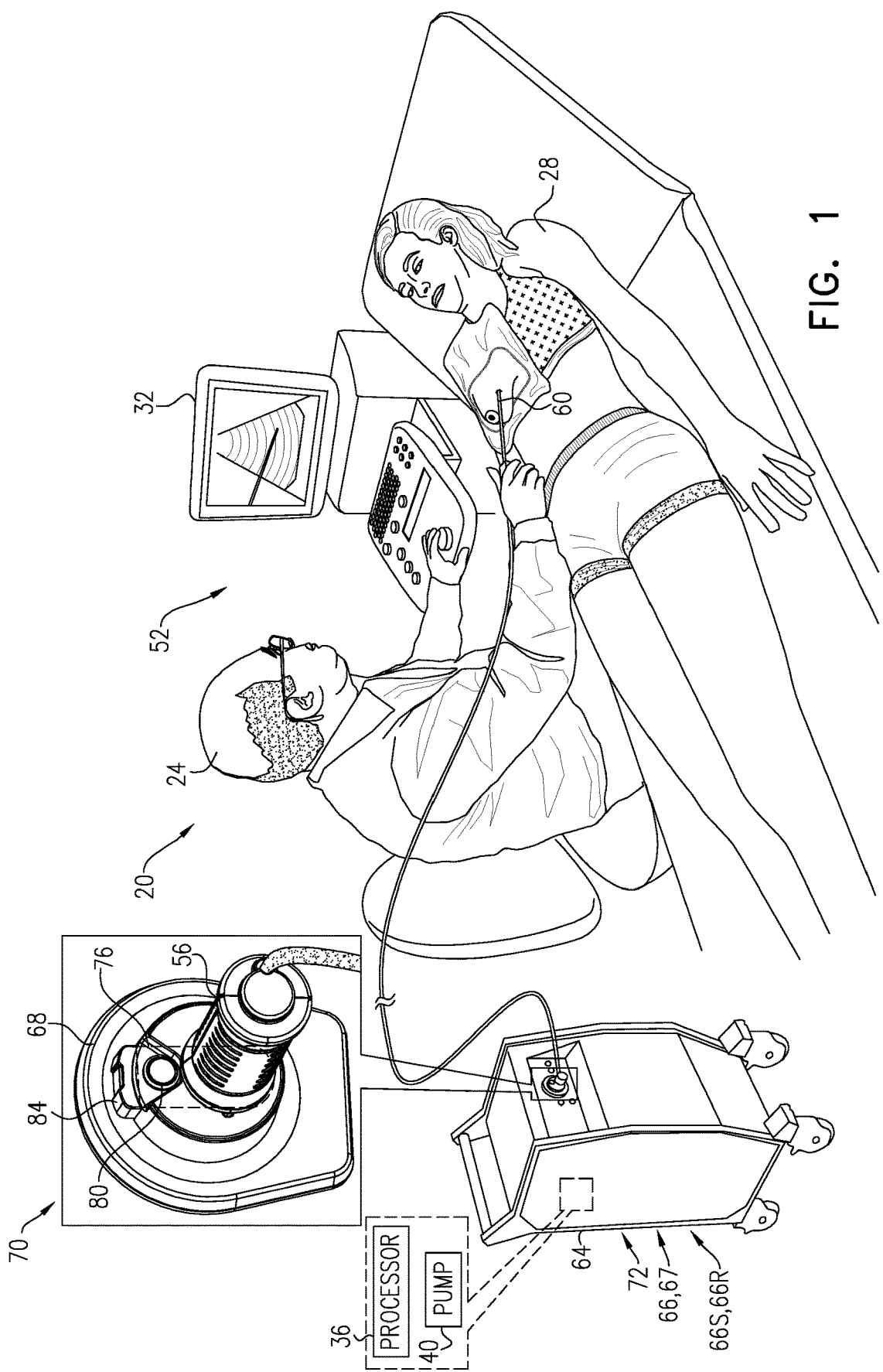
FIG. 1 is a schematic illustration of an apparatus being used for a cryogenic medical procedure, according to an embodiment of the present invention.

In a medical cryogenic procedure, it is important, from a safety point of view, to maintain the cryogen isolated and sealed from the surgeon performing the procedure, and from the patient undergoing the procedure, so that neither have any direct exposure to the cryogen. The procedure typically involves connecting and disconnecting a probe, which in some embodiments may be a sterile disposable probe, used for the procedure from a Dewar storing the cryogen, and at both times there may be leakage of the cryogen. In addition, when the probe is disconnected from the Dewar, it is important to seal the connection to the Dewar to reduce evaporation of the cryogen, to prevent ice forming on the connection, and to prevent expulsion of the cryogen from the Dewar. While speed and simplicity of operation is important for connecting and disconnecting the probe, as well as for sealing the connection, it is equally important, if not more so, that these actions cannot occur inadvertently.

Embodiments of the invention address these considerations by providing a connector to a Dewar storage unit that has a pump for the stored cryogen. The connector, together with a latch incorporated in the connector, has three states: a sealed state, which has a sealing plug in the connector, an active state, when the probe is in the connector, and an intermediate state when neither the sealing plug nor the probe are in the connector. Change from the intermediate state to either the sealed state or the active state, by respective insertion of the sealing plug or the probe into the connector, is fast and simple, and may be accomplished with only one hand. Once inserted, the latch locks the probe or the plug in place, so that inadvertent removal is not possible.

In addition, for safety, there is an activation mechanism attached to the latch so that removal of the plug or the probe requires initially operating the mechanism with two fingers of one hand, so as to free the plug or probe. Once freed, the other hand may extract the plug or probe. Also for safety, the mechanism is configured to detect the presence of the plug and the probe when they are inserted into the connector, by activating respective sensors indicating the presence of the plug or of the probe. Detection of the presence of the plug renders the Dewar pump inoperative, but when the presence of the probe is detected, the pump may be operated.

DETAILED DESCRIPTION

In the following description, like elements in the drawings are identified by like numerals. In addition, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Reference is now made to FIG. 1, which is a schematic illustration of an apparatus 20 being used for a cryogenic medical procedure, according to an embodiment of the present invention. By way of example the procedure assumed in the following description is on a breast tumor, but it will be understood that apparatus 20 may be used for other procedures, such as on a prostate or kidney tumor, and all such procedures are considered to be comprised within the scope of the present invention.

The procedure is performed by a physician 24 on a patient 28, and the physician has inserted a distal end 52 of a probe 60 into the patient. Typically, probe 60 is non-disposable, as is assumed in the following description. In some embodiments probe 60 comprises a sterile disposable probe, and those having ordinary skill in the art will be able to adapt the following description, mutatis mutandis, for this type of probe. The physician may observe an image of the procedure on a screen 32.

A proximal termination 56 of the probe is inserted into an opening 70 in a connector 68 of a cryogen storage unit 64. Storage unit 64 is operated by a processor 36, and, inter alia, comprises a cryogen pump 40 and a cryogen delivery section 66, both of which are under control of the processor. In one embodiment delivery section 66 comprises a cylindrical lumen 67, also herein termed a conduit 67, having a plurality of different diameters. Section 66 and conduit 67 are illustrated in FIG. 2B.

Figure 3:
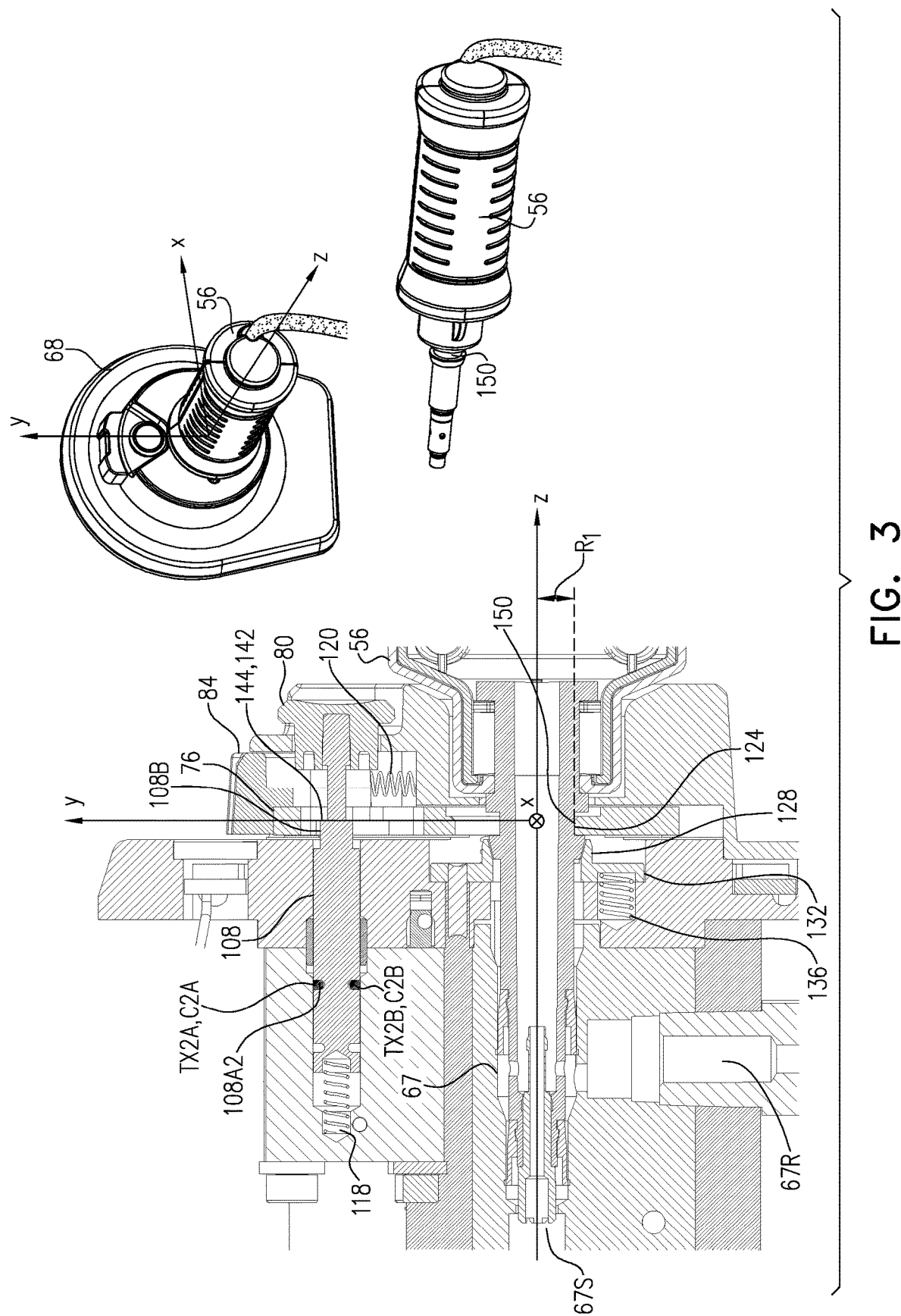
FIG. 3 is a schematic drawing of the connector when a proximal termination of a probe is inserted into the connector, according to an embodiment of the present invention.

A distal end of termination 56 is configured to mate with conduit 67, the distal end acting as a male section and the lumen as a female section. Once mated, the combination forms a cylindrical supply lumen 67S and a tubular return lumen 67R, and which may be used for delivery and return of cryogen. (Lumens 67S and 67R are illustrated in FIG. 3.) Thus, cryogen 72 contained in the storage unit may be delivered via supply lumen 67S and the proximal end, through the probe, to the distal end. Cryogen returns from the distal end via the probe and the proximal end and return lumen 67R to the storage unit.

During the procedure it is important that proximal termination 56 is not removed from connector 68. Such removal, typically inadvertent, may cause cryogen to escape from lumens 67S and 67R and/or proximal termination 56. Such an escape is a safety hazard. To prevent inadvertent removal, once the proximal termination has been inserted into the connector and mated with the lumens, a latch plate 76 in the connector automatically locks the proximal termination to the connector. As a further safety aspect, unlocking of the proximal termination from the connector, permitting removal of the proximal termination, may only be implemented positively, by simultaneous actuation of a button 80 and a latch plate retainer 84, the retainer being fixedly attached to the latch plate. The construction and operation of the latch plate in connector 68 is described in more detail with respect to FIGS. 2A, 2B, below.

Figure 2A:
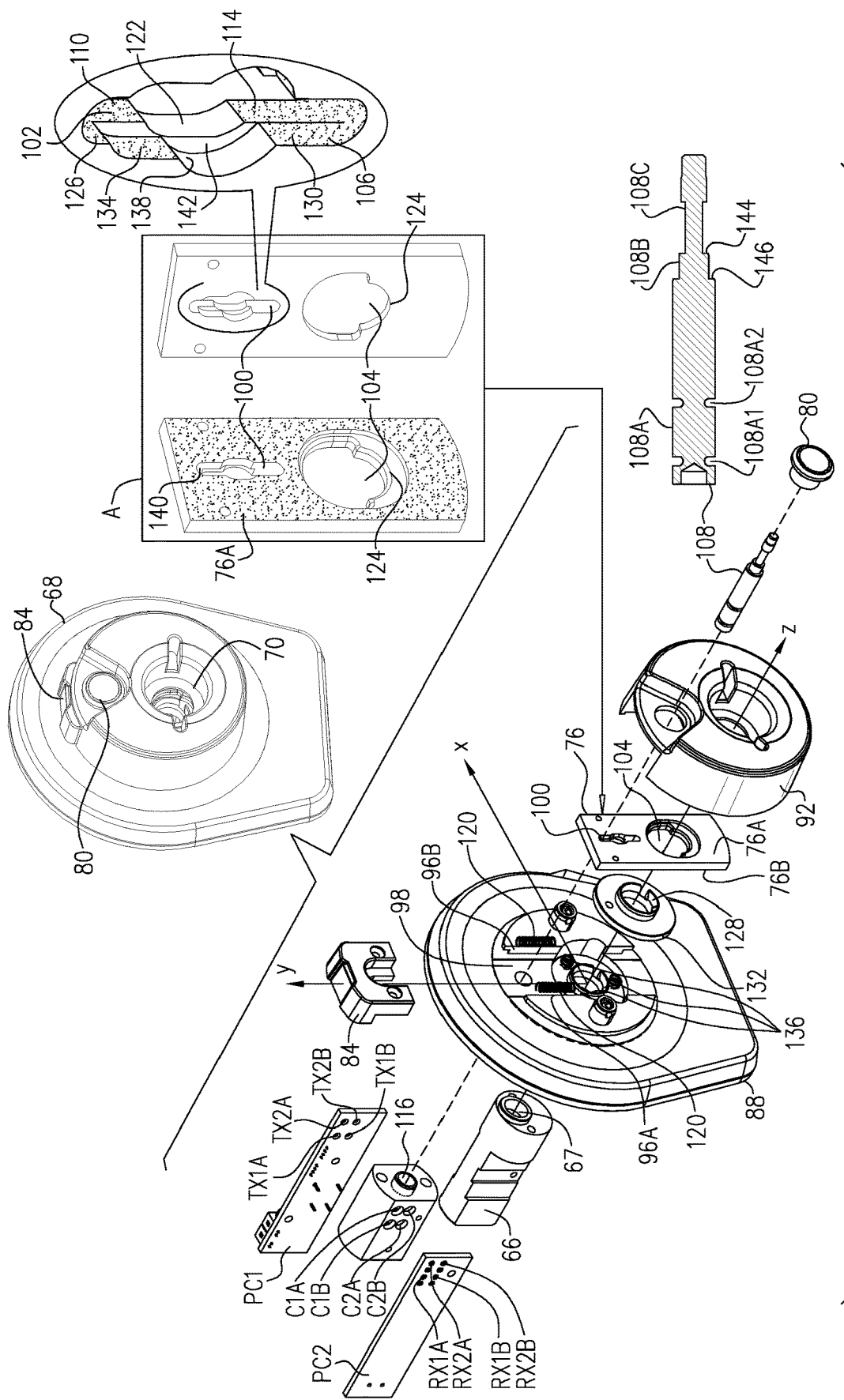
FIGS. 2A and 2B are schematic drawings of a connector of the apparatus, according to an embodiment of the present invention.
Figure 2B:
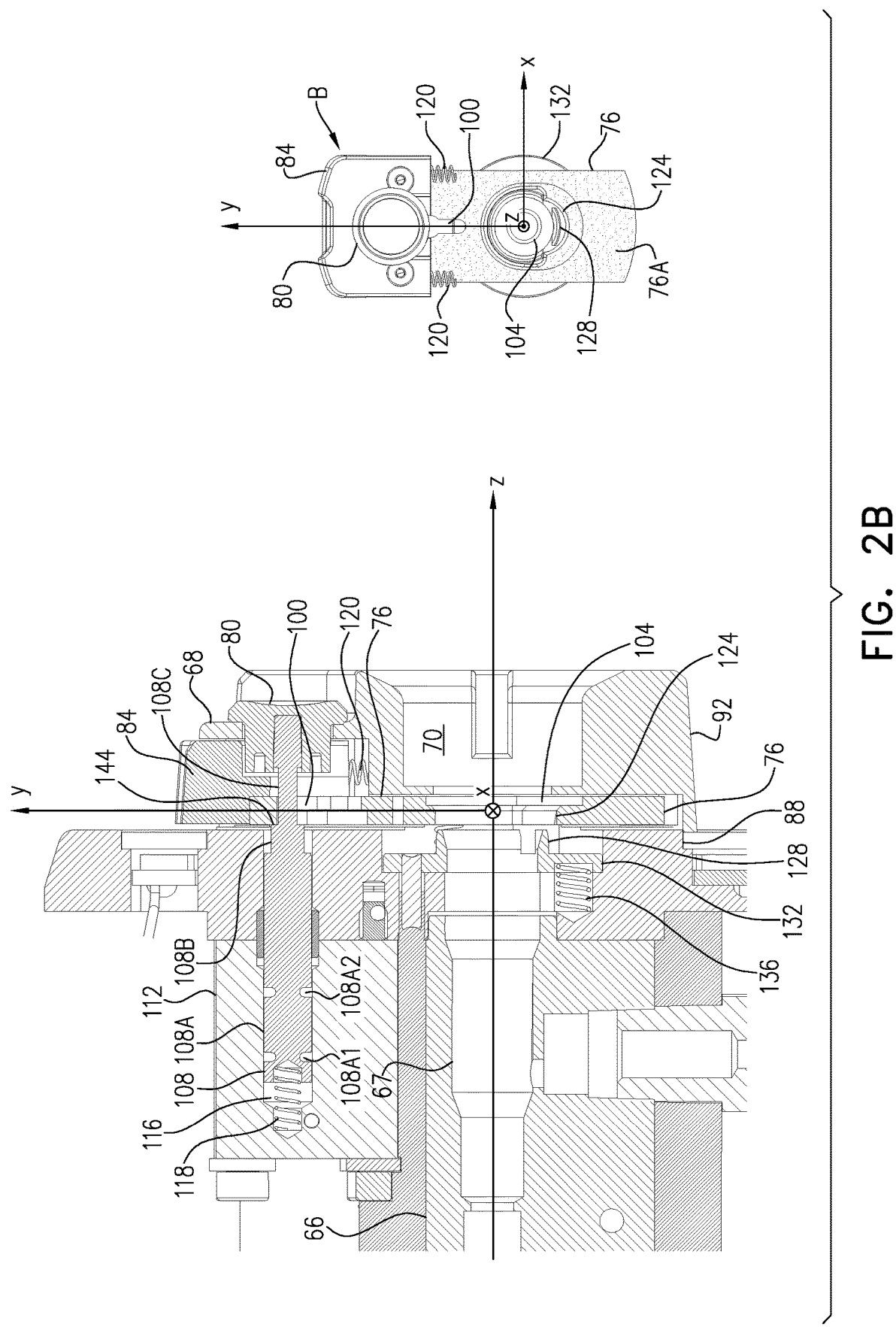

FIGS. 2A and 2B are schematic drawings of connector 68, according to an embodiment of the present invention. The figures illustrate the connector in a number of different views, without proximal termination 56 being inserted into the connector. A callout "A" also illustrates two opposing faces 76A, 76B of latch plate 16, and a figure "B" illustrates a front view of the latch.

For clarity in the description herein, connector 68 is assumed to be drawn on a set of xyz orthogonal axes. In a disclosed embodiment, the z axis is assumed to be collinear with the axis of symmetry of lumen 67 and to have a positive direction that extends proximally and horizontally from section 66. Latch plate 76 is formed, in a disclosed embodiment, as a generally rectangular plate that is normal to the z axis, and that has edges that are assumed to be vertical and horizontal. The positive y axis is assumed to be parallel to a vertical edge of plate 76, directed up; the positive x axis is assumed to be parallel to a horizontal edge of plate, directed right when viewed distally along the z axis. An origin of the axes is assumed to reside in the plate. It will be appreciated that the orientations described herein are for clarity and by way of example, and that embodiments of the present invention may function in substantially any orientation.

Latch plate 76 is held between a connector base plate 88, lying in an xy plane, and a connector cover 92. In base plate 88 are two shoulders, 96A 96B, both parallel to the y-axis and protruding from the plate in a positive z-direction, separated by the width of the latch plate, and the latch plate is positioned between the shoulders. The shoulders constrain the plate to move in a slot 98, between the shoulders, parallel to the y-axis. (Because it is attached to plate 76, plate retainer 84 also moves parallel to the y-axis.

Latch plate 76 has two apertures formed within the plate: a generally slot-like aperture 100, parallel to the y-axis, and a generally oval aperture 104 which is penetrated by the z-axis. More details of the structure and the function of the apertures are given below.

A cylindrical rod 108 (shown also in cross-section in the figure), which is formed as a plurality of solid cylinders 108A, 108B, 108C, of different diameters, penetrates slot-like aperture 100. Cylinder 108A has two circular grooves 108A1, 108A2 formed in the cylinder. There is a shoulder 146 between cylinder 108A and cylinder 108B, and a shoulder 144 between cylinders 108B and 108C.

Aperture 100 has two different slots 102, 106, each slot having a depth that is half the thickness of plate 76. Slot 102 has two different widths, an upper part 110 and a lower part 114 having a width corresponding to the diameter of cylinder 108C, and a central part 122 having a width corresponding to the diameter of cylinder 108B. Slot 106 is in four different sections, an upper section 126 and a lower section 130, both terminating in a semicircle and having a width corresponding to the diameter of cylinder 108C, an upper middle section 134 having the diameter of cylinder 108B, and a partially circular lower middle section 138, having a diameter equal to the diameter of cylinder 108A. There is an internal surface 142 in plate 76, formed by the different widths of the two slots.

Button 80 connects to a proximal end of cylindrical rod 108. A distal end of the rod is held within a rod holder 112, which is fixed to base plate 88. The rod holder has a blind hole 116 having a diameter corresponding to the diameter of cylinder 108A of rod 108, and there is a spring 118 within the blind hole contacting the rod distal end, the spring pushing the rod in a positive z-direction. It will be appreciated that rod 108 is able to slide in hole 116 in a z-direction.

Rod holder 112 acts as a support for two printed circuit (PC) boards PC1, PC2. Board PC1 has two pairs of radiation transmitters TX1A, TX1B, and TX2A, TX2B, herein by way of example assumed to comprise infra-red emitters. Board PC2 has two pairs of receivers RX1A, RX1B, and RX2A, RX2B configured to receive the radiation transmitted by the transmitters. Herein by way of example the receivers are assumed to comprise phototransistors. There are four channels C1A, C1B, C2A, C2B, in holder 112, and transmitters TX1A, TX1B, TX2A, TX2B are aligned respectively with channels C1A, C1B, C2A, C2B and with receivers RX1A, RX1B, and RX2A, RX2B. Thus, absent any obstruction in the channels, radiation from the transmitters is received by, and activates the receivers.

As is described below, cylinder 108A does obstruct the channels, except when grooves 108A1 or 108A2 align with a channel.

As is explained further below, receivers RX1A, RX1B, RX2A, RX2B, act as sensors, and are also termed herein sensors RX1A, RX1B, RX2A, RX2B. Sensors RX1A, RX1B, RX2A, RX2B detect, inter alia, the position of latch plate 76 in slot 98.

As stated above, latch plate 76 is constrained to move in a y-direction, in slot 98, by shoulders 96A, 96B. The plate is pushed in a positive y-direction by springs 120, which are held between plate retainer 84 and cover 92. In the state illustrated in FIGS. 2A and 2B, i.e., where proximal termination 56 is not in the connector, the plate is prevented from moving in a y-direction by a semicircular section 124 of aperture 104 contacting a circular split lip 128 protruding in a z-direction from a latch backing disc 132. Disc 132 and split lip 128 are maintained in contact with plate 76 by springs 136, which push the disc in a positive z direction, and which permit the disc to move along the z axis.

In the situation illustrated in FIGS. 2A and 2B, latch plate 76 is in its lowest possible y-position. In the illustrated situation an upper semicircular section 140 of section 126 mates with cylinder 108C of rod 108. In addition, by virtue of the force exerted in the positive z direction by spring 118 on rod 108, shoulder 144 between cylinder 108B and cylinder 108C is pushed against face 76B of plate 76. Consequently, rod 108 is fixed in a position where it is unable to move parallel to the z-axis. In this position, neither groove 108A1 nor groove 108A2 align with any of channels C1A, C1B, C2A, C2B. Rather, the channels are obstructed by cylinder 108A, so that none of sensors RX1A, RX1B, RX2A, RX2B, activate.

As is described below, in embodiments of the invention, plate 76 and rod 108 are in other positions, but in the situation illustrated in FIGS. 2A and 2B, where there is nothing inserted in aperture 104, latch plate 16 is in its lowest possible y-position, and rod 108 is in its most distal position measured parallel to the z axis.

FIG. 3 is a schematic drawing of connector 68 when proximal termination 56 of probe 60 is inserted into the connector, according to an embodiment of the present invention. The figure illustrates the connector and the termination in a perspective view, substantially as shown in FIG. 1 and in a cross-section view. The figure also illustrates the connector in a perspective view.

Termination 56 fits within conduit 67, forming cylindrical supply lumen 67S and connecting to tubular return lumen 67R. Termination 56 has an axis of symmetry that, when it is in the conduit 67, is collinear with the z-axis. On insertion of termination 56 into opening 70, the termination pushes lip 128 and its latch backing disc 132 in a negative z-direction against springs 136, so that the lip disengages from semi-circular opening 124. The disengagement permits latch plate 76 to move in a y-direction, and springs 120 push the plate in a positive y-direction.

Latch plate 76 moves in a positive y-direction until opening 124 engages with a circular groove 150 in termination 56. The engagement grips the termination, and locks it in place so that the termination may not be removed from opening 70, except as described below. Groove 150 has a radius $R_1$, and it will be appreciated that it is the value of $R_1$ that determines the location of latch plate 76 when termination 56 is in place, and so determines the distance moved by the latch plate when the termination is inserted into opening 70.

The vertical movement of latch plate 76 causes shoulder 144 of rod 108 to slide in slot-like aperture 100 against face 16B of the latch plate. While shoulder 144 slides against face 76B, the sliding continues until the slot that rod 108 is in enlarges, at section 134 (FIG. 2A); at this point spring 118 pushes rod 108 in a positive z-direction until shoulder 144 contacts internal surface 142.

The positive z-direction movement of rod 108 causes groove 108A2 to align with channels C2A and C2B, so that the channels are not obstructed. (Channels C1A and C1B are obstructed by cylinder 108A.) Consequently transmitters TX2A and TX2B activate respective sensors RX2A and RX2B. The sensor activation acts as a positive indication that termination 56 has been inserted into opening 70. The positive indication from the sensors may be used by delivery section 66 to recognize that it is safe to permit flow of cryogen from storage unit 64, and thus to activate the delivery section. As is described further below, deactivation of the sensors prevents cryogen flow.

To remove termination 56 from opening 70, the termination must be disengaged from latch plate 76. The disengagement requires the latch plate to move down, so that circular groove 150 is no longer gripped by the latch plate, but in the state illustrated in FIG. 3 this is not possible, since cylinder 108B contacts an upper part of upper middle section 134.

Embodiments of the invention provide a two step method for removal of termination 56. As a first step button 80 is pushed in, typically by one finger or a thumb of physician 24, so that cylinder 108B no longer contacts an upper part of upper middle section 134. Springs 120 still maintain the latch plate gripping groove 150, but the removal of contact between cylinder 108B and section 134, permits a second step.

In the second step, the physician uses a second of his/her digits to press down on plate retainer 84, so that latch plate 76 moves in a negative y-direction, and disengages from groove 150 of the termination. The physician may then remove the termination.

It will be understood that the first step, of pushing button 80 in, deactivates sensors RX2A and RX2B, by blocking the channels to the sensors. The sensor deactivation may be used to deactivate cryogen delivery section 66 of cryogen unit 64 and operation by processor 36 of pump 40, so preventing cryogen flow from the section and from the unit. It will also be understood that inadvertent pushing of button 80 and pressing retainer 84 deactivates sensors RX2A and RX2B, and thus halts cryogen flow by deactivating delivery section 66 and pump 40.

Figure 4:
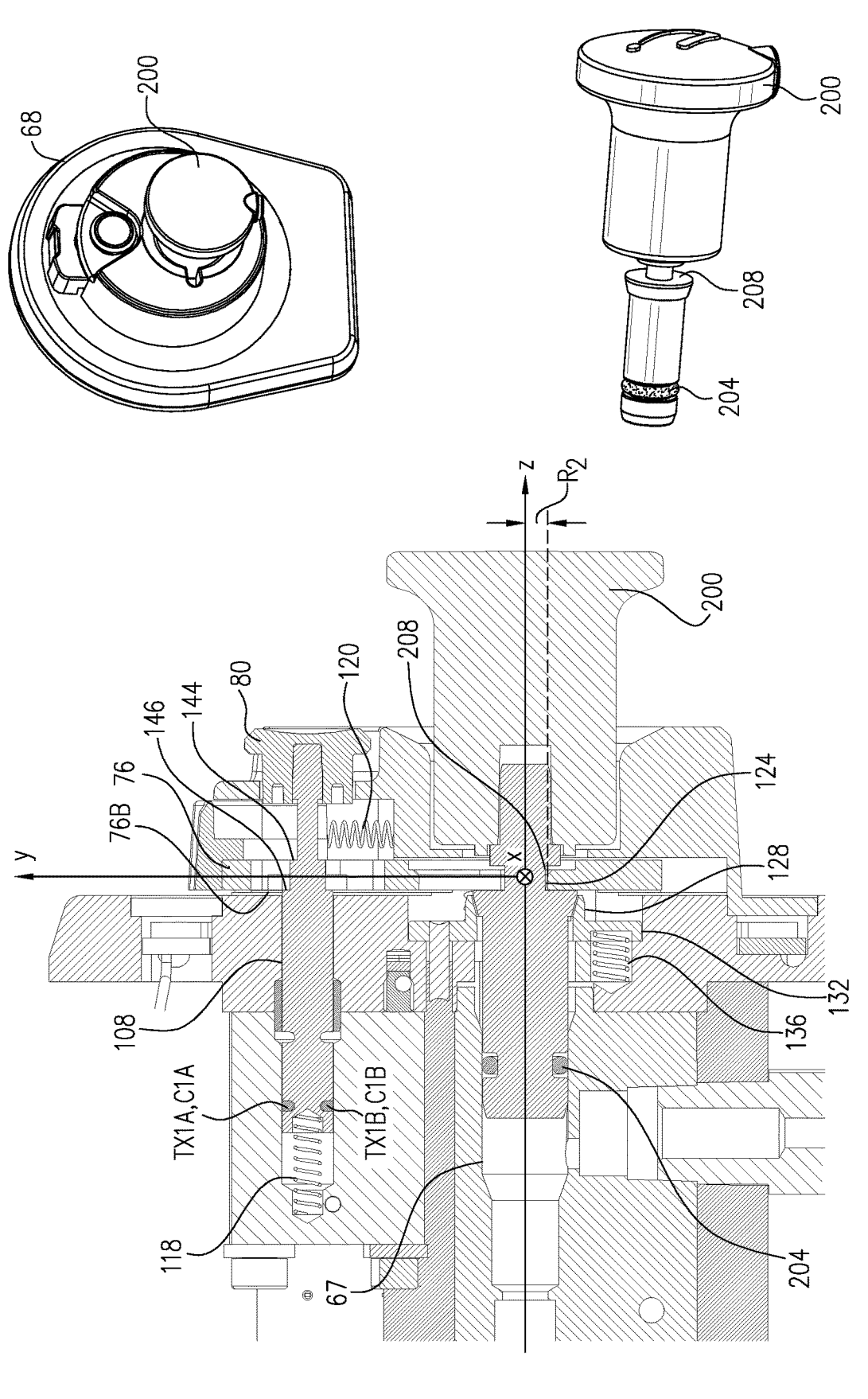
FIG. 4 is a schematic drawing of the connector when a sealing plug is inserted into the connector, according to an embodiment of the present invention.

FIG. 4 is a schematic drawing of connector 68 when a sealing plug 200 is inserted into the connector, according to an embodiment of the present invention. The figure illustrates the connector and the plug in a perspective view, substantially as shown in FIG. 1 and in a cross-section view. The figure also illustrates the connector in a perspective view.

When probe 60 is not in use, cryogen unit 64 may be sealed by plug 200, in order to prevent air and/or moisture entering the unit, as well as to reduce the evaporation of any cryogen in the unit, and to prevent any uncontrolled release of cryogen.

Plug 200 fits within lumen 67, being held in the lumen by an O-ring 204, and the plug has an axis of symmetry that, when it is in the lumen, is collinear with the z-axis. On insertion of plug 200 into opening 70, the plug pushes lip 128 and its latch backing disc 132 in a negative z-direction against springs 136, so that the lip disengages from semi-circular opening 124. The disengagement permits latch plate 76 to move in a y-direction, and springs 120 push the plate in a positive y-direction.

Latch plate 76 moves in a positive y-direction until opening 124 engages with a circular groove 208 in plug 200. The engagement grips the plug, and locks it in place so that the plug may not be removed from opening 70, except as described below. Groove 208 has a radius $R_2$, and it will be appreciated that it is the value of $R_2$ that determines the location of latch plate 76 when plug 200 is in place, and so determines the distance moved by the latch plate when the plug is inserted into opening 70. In embodiments of the invention, $R_1$ and $R_2$ are configured to be different, and in the disclosed embodiment, $R_2 < R_1$.

For the case when $R_2 < R_1$, shoulder 144 initially slides as described above for termination 56 (FIG. 3). Because $R_2 < R_1$, the possible vertical motion of the latch plate is larger than is the case with the termination. Consequently latch plate 76 continues moving vertically upwards until rod 108 is able to enter central part 122 of slot 102 (FIG. 2A). When it enters the central section, spring 118 pushes the rod in a positive z-direction until shoulder 146 contacts face 76B of the latch plate. In this case cylinder 108B contacts an upper part of central section 122, and this contact prevents the latch plate from moving down.

The positive z-direction movement of rod 108 causes groove 108A1 to align with channels C1A and C1B, so that the channels are not obstructed. (Channels C2A and C2B are now obstructed by cylinder 108A.) Consequently transmitters TX1A and TX1B activate respective sensors RX1A and RX1B. The sensor activation acts as a positive indication that plug 200 has been inserted into opening 70.

Typically, when apparatus 20 is powered on, processor 36 checks, using sensors RX1A and RX1B that plug 200 is in place, so that, after removal of the plug, termination 56 of probe 60 may be inserted into the connector. In addition, on shutting down, processor 36 may check, using the sensors, that plug 200 is in place, so as to enable an orderly shutdown.

As for termination 56, embodiments of the invention provide a two step method for removal of plug 200. As a first step button 80 is pushed in, as for termination 56, typically by physician 24 using one of his/her digits. In the second step, which is now permitted since the first step enables the latch plate to be moved vertically, the physician uses a second digit to press down on plate retainer 84, so that latch plate 76 moves in a negative y-direction, and disengages from groove 208 of the plug. The physician may then remove the plug.

It will be understood that the first step, of pushing button 80 in, deactivates sensors RX1A and RX1B, by blocking the channels to the receivers.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Cryogenic apparatus, comprising:
a connector comprising:
a connector base plate configured for connection to a conduit carrying a cryogen;
a slot extending across the base plate; and
a connector cover, comprising a first cover opening and a second cover opening, coupled to the base plate;
a plug, which is configured for insertion via the first cover opening into an opening in the base plate;
a latch plate configured to slide within the slot between a first position, in which the plug is inserted through an aperture in the latch plate into the opening, and a second position, in which a cryogenic probe is inserted via the first cover opening through the aperture and brought into fluid communication with the opening;
a sensor, which is coupled to control a flow of the cryogen through the conduit by detecting whether the latch plate is in the first position or the second position;
a control rod which penetrates the second cover opening and a further aperture in the latch plate and which is configured to operate the sensor; and
a button, attached to a termination of the control rod so as to lie outside the connector cover.

2. The cryogenic apparatus according to claim 1, wherein the plug comprises a groove, and wherein the aperture grips the groove, when the plug is inserted through the aperture, so as to lock the plug to the latch plate.

3. The cryogenic apparatus according to claim 1, wherein the cryogenic probe comprises a groove, and wherein the aperture grips the groove, when the probe is inserted through the aperture, so as to lock the probe to the latch plate.

4. The cryogenic apparatus according to claim 1, wherein the control rod, when the latch plate is in the first position, is in a first control rod position that deactivates the sensor so as to prevent flow of the cryogen, and when the latch plate is in the second position, is in a second control rod position that activates the sensor so as to permit flow of the cryogen.

5. The cryogenic apparatus according to claim 1, wherein the control rod when the latch plate is in the first position, is in a first control rod position that prevents the latch plate from moving from the first position, and when the latch plate is in the second position, is in a second control rod position that prevents the latch plate from moving from the second position.

6. The cryogenic apparatus according to claim 5, wherein the control rod, when translated from the first control rod position permits the latch plate moving from the first position, and, when translated from the second control rod position permits the latch plate moving from the second position.

7. The apparatus according to claim 1, wherein the cover comprises a third cover opening, the apparatus further comprising a latch plate retainer fixedly attached to the latch plate and protruding through the third cover opening.

8. A method, comprising:
providing a connector comprising:
a connector base plate configured for connection to a conduit carrying a cryogen;
a slot extending across the base plate; and
a connector cover, comprising a first cover opening and a second cover opening, coupled to the base plate;
configuring a plug for insertion via the first cover opening into an opening in the base plate;
sliding a latch plate within the slot between a first position, in which the plug is inserted through an aperture in the latch plate into the opening, and a second position, in which a cryogenic probe is inserted via the first cover opening through the aperture and brought into fluid communication with the opening;
coupling a sensor to control a flow of the cryogen through the conduit by detecting whether the latch plate is in the first position or the second position;
providing a control rod which penetrates the second cover opening and a further aperture in the latch plate and which is configured to operate the sensor; and
attaching a button to a termination of the control rod so as to lie outside the connector cover.

9. The method according to claim 8, wherein the plug comprises a groove, and wherein the aperture grips the groove, when the plug is inserted through the aperture, so as to lock the plug to the latch plate.

10. The method according to claim 8, wherein the cryogenic probe comprises a groove, and wherein the aperture grips the groove, when the probe is inserted through the aperture, so as to lock the probe to the latch plate.

11. The method according to claim 8, wherein the control rod, when the latch plate is in the first position, is in a first control rod position that deactivates the sensor so as to prevent flow of the cryogen, and when the latch plate is in the second position, is in a second control rod position that activates the sensor so as to permit flow of the cryogen.

12. The method according to claim 8, wherein the control rod, when the latch plate is in the first position, is in a first control rod position that prevents the latch plate from moving from the first position, and when the latch plate is in the second position, is in a second control rod position that prevents the latch plate from moving from the second position.

13. The method according to claim 12, wherein the control rod, when translated from the first control rod position permits the latch plate moving from the first position, and, when translated from the second control rod position permits the latch plate moving from the second position.

14. The method according to claim 8, wherein the cover comprises a third cover opening, the method further comprising fixedly attaching a latch plate retainer to the latch plate so as to protrude through the third cover opening.

* * * * *